US009512474B2

(12) United States Patent
Seone et al.

(10) Patent No.: US 9,512,474 B2
(45) Date of Patent: Dec. 6, 2016

(54) MOLECULAR TARGETS AND METHODS FOR FORMULATION SCREENING AND PRESERVATIVE EFFICACY TESTING

(71) Applicant: LONZA WALKERSVILLE INC., Walkersville, MD (US)

(72) Inventors: Sophie Seone, Cournon D'Auvergne (FR); Stephanie Gontard, Dallet (FR); Timothy Coleman, Derwood, MD (US)

(73) Assignee: LONZA WALKERSVILLE, INC., Walkersville, MD (US)

( * ) Notice: Subject to any disclaimer, the term of this patent is extended or adjusted under 35 U.S.C. 154(b) by 0 days.

(21) Appl. No.: 14/342,171

(22) PCT Filed: Sep. 28, 2012

(86) PCT No.: PCT/US2012/057705
§ 371 (c)(1),
(2) Date: Feb. 28, 2014

(87) PCT Pub. No.: WO2013/049437
PCT Pub. Date: Apr. 4, 2013

(65) Prior Publication Data
US 2014/0272977 A1 Sep. 18, 2014

Related U.S. Application Data

(60) Provisional application No. 61/540,006, filed on Sep. 28, 2011.

(51) Int. Cl.
*C12Q 1/68* (2006.01)
(52) U.S. Cl.
CPC .............. *C12Q 1/686* (2013.01); *C12Q 1/689* (2013.01); *C12Q 1/6895* (2013.01)
(58) Field of Classification Search
None
See application file for complete search history.

(56) References Cited

U.S. PATENT DOCUMENTS

| 5,726,021 A | 3/1998 | Britschgi et al. | |
| 6,472,149 B1 | 10/2002 | Gendre et al. | |
| 6,738,502 B1 * | 5/2004 | Coleman et al. | G01N 21/274 382/133 |

FOREIGN PATENT DOCUMENTS

| DE | WO 2009037279 A1 * | 3/2009 | ............ C07K 14/415 |
| EP | 1950313 A2 | 7/2008 | |
| WO | 2007/120669 A2 | 10/2007 | |
| WO | 2010/068802 A1 | 6/2010 | |
| WO | WO 2010068802 A1 * | 6/2010 | ............... C12Q 1/02 |
| WO | 2011/109901 A1 | 9/2011 | |

OTHER PUBLICATIONS

Stratagene (Gene Characterization Kits; 1988).*
Weiner et al. (Kits and their unique role in molecular biology: a brief retrospective, BioTechniques 44:701-704 (25th Anniversary Issue, Apr. 2008)).*
Lu et al. (Reverse Transcription of 16S rRNA to Monitor Ribosome-Synthesizing Bacterial Populations in the Environment, Appl. Environ. Microbiol. Jul. 2009 vol. 75 No. 13 4589-4598).*
Kempsell et al. (The nucleotide sequence of the promoter, 16s rRNA and spacer region of the ribosomal RNA operon of *Mycobacterium tuberculosis* and comparison with *Mycobacterium leprae* precursor rRNA, J Gen Microbiol. Aug. 1992;138 Pt 8:1717-27).*
Cui et al. (Estimation of ribosomal RNA transcription rate in situ, Biotechniques. Jan. 2004;36(1):134-8).*
Lu et al. (Quantification of In Situ Growth Activity: A Novel Approach to Study Response of Activated Sludge to Toxic Shock Loadings, Proceedings of the Water Environment Federation, WEFTEC 2006: Session 61 through Session 70, pp. 5000-5007(8), Dec. 1, 2006).*
Cangelosi et al. (Molecular Detection of Viable Bacterial Pathogens in Water by Ratiometric Pre-rRNA Analysis, Appl. Environ. Microbiol. Feb. 2010 vol. 76 No. 3 960-962).*
Oerther et al. (Elevated precursor 16s rrna levels suggest the presence of growth inhibitors in wastewater, Water Sci Technol. 2003;47(11):241-50, Dec. 31, 2003).*
Cagelosi et al. (Detection of Stable Pre-rRNA in Toxigenic Pseudo-nitzschia Species, Appl Environ Microbiol. Dec. 1997;63(12):4859-65).*
Oerther et al. (Monitoring Precursor 16S rRNAs of *Acinetobacter* spp. In Activated Sludge Wastewater Treatment Systems, Appl Environ Microbiol. May 2000;66(5):2154-65).*
Aellen, S., et al.: "Detection of Live and Antibiotic-Killed Bacteria by Quantitative Real-Time PCR of Specific Fragments of rRNA." Antimicrobial Agents and Chemotherapy, vol. 50, No. 6, Jun. 1, 2006, pp. 1913-1920, XP055043984.
Cangelosi, G.A., et al.: "Molecular Detection of Viable Bacterial Pathogens in Water by Ratiometric Pre-rRNA Analysis." Applied and Environmental Microbiology, vol. 76, No. 3, Feb. 1, 2010, pp. 960-962, XP055043960.
Cenciarini-Borde, C., et al.: "Nucleic acids as viability markers for bacteria detection using molecular tools." Future Microbiology, vol. 4, No. 1, Feb. 1, 2009, pp. 45-64, XP008119055.
Szabo, E.A., et al.: "Detection of *Salmonella enteritidis* by reverse transcription-polymerase chain reaction (PCR)." International Journal of Food Microbiology, vol. 51, No. 2-3, Oct. 1, 1999, pp. 113-122, XP055046732.

* cited by examiner

*Primary Examiner* — Aaron Priest
(74) *Attorney, Agent, or Firm* — Gianna Julian-Arnold; Saul Ewing LLP

(57) ABSTRACT

Methods and kits are disclosed for distinguishing viable from nonviable microbial cells. The methods and kits are useful in the screening of cell culture formulations and the testing of preservative efficacy. The methods involve the amplification and quantitation of microbe-specific DNA from precursor rRNA or Elongation Factor 3 mRNA in treated versus nontreated test samples using the reverse transcription polymerase chain reaction.

19 Claims, 7 Drawing Sheets

MOLECULAR TARGETS AND METHODS FOR FORMULATION SCREENING AND PRESERVATIVE EFFICACY TESTING

CROSS REFERENCE TO RELATED APPLICATIONS

This application claims the priority of PCT/US2012/057705, filed on Sep. 28, 2012, which claims the benefit of priority to U.S. Application No. 61/540,006, filed on Sep. 28, 2011, the entire contents of each of which are hereby incorporated in total by reference.

FIELD OF THE INVENTION

The present invention relates to a method and kit for distinguishing viable from non-viable cells. Specifically, the present invention relates to a method and kit for identifying microbial RNA targets (precursor rRNA (pre-rRNA) or messenger RNA (mRNA)) in microbes (such as bacteria, yeasts or molds) that can serve as indicators of cell viability in preservative screening or Preservative Efficacy Testing (PET).

BACKGROUND OF THE INVENTION

There is often a need to distinguish viable cells from non-viable or inactivated cells. For example, one may wish to distinguish viable bacteria from non-viable bacteria in patient specimens. Similarly, distinguishing viable cells from non-viable cells can have application in cosmeceutical research/testing, pharmaceutical release testing, testing related to water purity/safety, and the like.

Currently, PET is assessed by conventional microbiological culture methods that combine enrichment/growth and plate counting. Time to results is very long. Depending on the preservative action, viable but non-cultivable cells are not detected by these culture methods. Furthermore, bacterial pathogens may be present in small numbers and/or bacterial samples may have poor plating efficiency that yields underestimates of performance.

Similarly, molecular methods like reverse transcription polymerase chain reaction (RT-PCR) assays targeting microbial rRNA are not able to clearly distinguish viable from non-viable organisms after treatment with preservative(s).

PCT/US2009/067565 (WO2010/068802) provides a ratiometric pre-rRNA analysis including compositions and methods for detecting the presence of viable cells in a sample. This disclosure describes nucleic acid amplification testing to detect species-specific pre-rRNA molecules. This method requires the use of two sample sets. A first sample set that is not stimulated to grow and a second sample set that is stimulated with nutrients/growth media prior to evaluation of the pre-rRNA targets. The level of pre-rRNA in the stimulated samples is compared to the level of pre-rRNA in the non-stimulated samples to obtain an indication of the presence of viable versus non-viable cells. As disclosed, only the viable cells respond to the exposure to nutrients by demonstrating an increase in pre-rRNA. This step is referred to in PCT/US2009/067565 as a ratiometric assay. Thus, PCT/US2009/067565 basically discloses pre-rRNA replenishment following nutrient stimulation as a basis for measuring viable microbial cells. A similar ratiometric approach can be used for an mRNA target.

US 2004/0265,934 discloses detection of pre-rRNA as a measure of bacteria viability in the identification of antibiotic drugs that reduce or inhibit rRNA transcription. Specifically, hybridization assay probes are disclosed for detecting a target sequence of rRNA of one or more mycobacteria optionally present in a sample. Thus, the disclosure of 2004/0265934 is not directed to detecting viable versus non-viable cells. Rather, this disclosure provides the use of probes directed to target sequences of mycobacterial rDNA, pre-rRNA, or rRNA.

Similarly, U.S. Pat. No. 5,770,373 discloses methods and oligonucleotide probe compositions for determining antibiotic resistance in mycobacteria. This method includes assaying the levels of pre-rRNA in the cells. The cells are treated by enzymatic or mechanical means to expose the cell membrane to lysis reagents; contacting the cells with the lysis reagent under conditions that release but do not degrade the mycobacterial pre-rRNA; and then detecting the mycobacterial pre-rRNA using an oligonucleotide probe. As disclosed, pre-rRNA is detected as a measure of sensitivity of mycobacterial cells to antimicrobial agents. This detection is accomplished through a biotinylated probe in a chemilluminescent sandwich hybridization assay.

WO/1998/018958 provides a method for detecting live microbiological contaminants in a food product sample. The invention describes a method for detecting live microbiological contaminants in food product samples which relies on detecting the presence of mRNA coding for Elongation Factor 1 alpha (EF-1α): a gene product involved in protein synthesis.

SUMMARY OF THE INVENTION

The present invention provides a method and kit for pre-rRNA and Elongation Factor 3 (EF-3) mRNA assays directed to the detection of viable versus non-viable microbial cells. The method and kit can be used on different platforms including but not limited to the microCompass™ system. The method and kit of the present invention has varying applications including but not limited to cosmeceutical research/testing, pharmaceutical release testing, water purification/safety testing, and the like.

In one embodiment of the invention, a method is provided for identifying and quantifying viable microbial cells in one or more samples containing a microorganism of interest. In one aspect, species-specific DNA is amplified from pre-rRNA-containing samples using a reverse transcription-polymerase chain reaction. The amplification step involves, for example, using a first primer complementary to a pre-rRNA region of a microorganism of interest, using a second primer complementary to a mature rRNA region of the microorganism of interest, and performing multiple cycles of amplification using the first primer and the second primer to yield detectable levels of amplified species-specific DNA. The quantitation step involves, for example, using a fluorescently labeled hybridizing probe complementary to the mature rRNA region of the microorganism of interest, using the first primer complementary to the pre-rRNA region of the microorganism of interest and the second primer complementary to the mature rRNA region of the microorganism of interest, and performing multiple cycles of amplification using the fluorescently labeled hybridizing probe and the first and the second primers to yield increasing levels of fluorescence signal above fluorescence background. The amplification of the species-specific DNA indicates the presence of viable microbial cells in one or more samples, and the quantitation of amplified species-specific DNA provides a relative measurement of the amount of viable microbial cells in one or more samples.

In certain aspects of the invention, the microorganisms of interest may be, for example, *Escherichia coli, Serratia marcescens*, or *Bacillus subtilis*, in which cases the first primers, second primers, and fluorescently labeled hybridizing probes are designed on the 3'-end of 16S rRNA.

In other aspects of the invention, the microorganisms of interest may be, for example, *Pseudomonas aeruginosa, Staphylococcus aureus*, or *Staphylococcus epidermidis*, in which cases the first primers, second primers, and the fluorescently labeled hybridizing probes are designed on the 5'-end of 23S rRNA.

In still other aspect of the invention, the microorganism of interest may be, for example, *Aspergillus brasiliensis*, in which case the first primer, the second primer, and the fluorescently labeled hybridizing probe are designed on the 5'-end of 5.8S rRNA.

In another aspect of the invention, the method may involve collecting cells onto a filter membrane and lysing the collected cells.

In another aspect, the method may involve applying the amplification step and the quantitation step to both a test sample and a control sample, the control sample containing non-treated cells and then comparing the relative measurement of the amount of viable microbial cells in the control samples to the relative measurement of the amount of viable microbial cells in the test sample.

It is anticipated that the method of the invention is applicable to, for example, samples of cell cultures containing one or more cell culture formulations or preservatives in need of screening or efficacy testing.

In another embodiment of the invention, a method is provided for identifying and quantifying viable microbial cells in one or more samples containing a microorganism of interest. In one aspect, species-specific DNA is amplified EF-3 mRNA-containing samples using a reverse transcription-polymerase chain reaction. The amplification step involves, for example, using a forward primer complementary to the EF-3 mRNA region of the microorganism of interest, using a reverse primer complementary to the EF-3 mRNA region of the microorganism of interest, and performing multiple cycles of amplification using the forward primer and the reverse primer to yield detectable levels of amplified species-specific DNA. The quantitation step involves, for example, using a fluorescently labeled forward hybridizing probe complementary to the EF-3 mRNA region of the microorganism of interest, using the forward and the reverse primers complementary to the EF-3 mRNA region of the microorganism of interest, and performing multiple cycles of amplification using the fluorescently labeled forward hybridizing probe and the forward and the reverse primers to yield increasing levels of fluorescence signal above fluorescence background. The amplification of the species-specific DNA indicates the presence of viable microbial cells in one or more samples, and the quantitation of the amplified species-specific DNA provides a relative measurement of the amount of viable microbial cells in one or more samples.

In one aspect, the microorganism of interest is *Candida albicans*.

In another aspect of the embodiment, the method may involve collecting cells onto a filter membrane and lysing the collected cells.

In another aspect of the embodiment, the method may involve applying the amplification step and the quantitation step to both a test sample and a control sample, the control sample containing non-treated cells and then comparing the relative measurement of the amount of viable microbial cells in the control samples to the relative measurement of the amount of viable microbial cells in the test sample.

It is anticipated that the method of the embodiment is applicable to, for example, samples of cell cultures containing one or more cell culture formulations or preservatives in need of screening or efficacy testing.

In still another embodiment of the invention, a method is provided for cell culture formulation screening or cell culture preservative efficacy testing in which one would perform the following steps: calibrating cells to a desired density; collecting cells on a filter membrane; applying nutrients to said membrane to yield enriched cells; incubating said enriched cells; removing nutrients; adding lysis buffer to membrane; recovering cell lysates; transferring lysate; extracting and purifying RNA; and amplifying and quantitating species-specific DNA by the reverse transcription-polymerase chain reaction.

In other embodiments of the invention, kits are provided for determining the presence of viable versus nonviable cells in a test sample. The kits contain, for example, primers and probes complementary to, for example, the 3'-end of 16S rRNA, the 5'-end of 23S rRNA, the 5'-end of 5.8S rRNA, and the mRNA of the EF-3 gene.

There have been thus been outlined, rather broadly, features of the invention in order that the detailed description thereof that follows may be better understood, and in order that the present contribution to the art may be better appreciated. There are, of course, additional features of the invention that will be described further hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other methods and systems for carrying out the several purposes of the present invention. It is important, therefore, that equivalent constructions insofar as they do not depart from the spirit and scope of the present invention, are included in the present invention.

For a better understanding of the invention, its operating advantages and the specific objects attained by its uses, reference should be had to the accompanying drawings and descriptive matter which illustrate preferred embodiments of the invention.

BRIEF DESCRIPTION OF THE DRAWINGS AND THE FIGURES

DETAILED DESCRIPTION OF THE INVENTION

Provided herein is a method and kit for identifying pre-rRNA and EF-3 mRNA in microbes such as bacteria, yeasts or molds. The method can be used, for example, to distinguish viable cells from non-viable or inactivated cells in response to a selected treatment with chemical or biological agents. As disclosed herein, RT-PCR is used to amplify species-specific DNA from pre-rRNA- or EF-3 mRNA-containing samples. This is subsequently quantitated in amplification cycles by detection of hybridized fluorescent probe. For the pre-rRNA assay, the amplification of target is achieved using one primer complementary to the pre-rRNA region of the specific microbe of interest and a second primer complementary to the mature rRNA region. The hybridization probe used for quantitation of amplified product is complementary to the amplified rRNA region. Amplification and quantitation only occur if pre-rRNA is present (i.e., pre-rRNA is abundant in actively growing bacteria). For the EF-3 mRNA assay, the amplification of target is achieved using two primers and a probe complementary to the mRNA region specific to the EF-3 gene. Amplification and quantification only occur if EF-3 mRNA are present (i.e., EF-3 mRNA is present in actively growing yeast). In an exemplary protocol further described herein, cells are collected onto a filter membrane by centrifugation and lysed thereon. RT-PCR data is compared in non-treated cells (e.g., live microbial cells) versus treated (e.g., by preservative) cells.

The pre-rRNA Assay

The correlation between the cellular pre-rRNA content and the growth rate is one of the earliest and most fundamental observations in microbial physiology. For example, in the bacteria *E. coli*, during rapid growth (where doubling time is less than one hour), over 50 percent of the total RNA produced is rRNA. Ribosome synthesis is therefore a central process in microbial growth.

Figure 1:
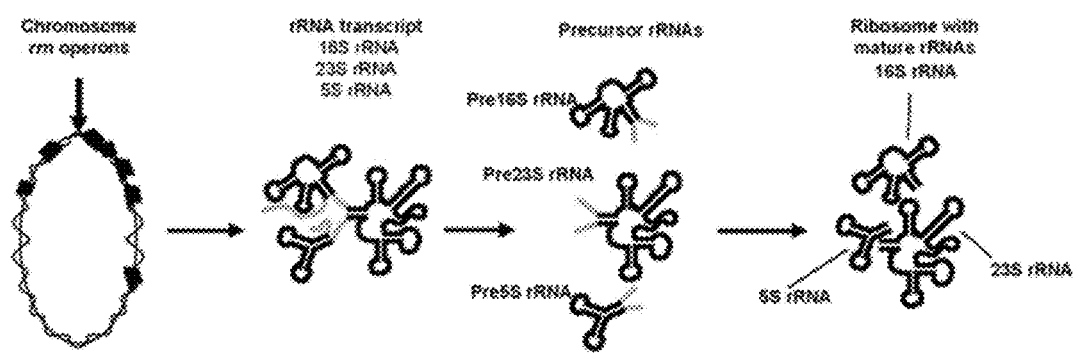
FIG. 1 illustrates the ribosome RNA synthesis and maturation model of *E. coli*.

Currently, the ribosome genesis model of *E. coli* is the most complete and is assumed to describe ribosome synthesis for most bacteria. As illustrated in FIG. 1, ribosome RNA synthesis and maturation in *E. coli* begins with transcription from the rrn operon, producing a polycistronic rrn transcript that is subsequently processed to release pre-rRNA molecules. Further processing and addition of ribosomal proteins results in the formation of fully mature rRNA molecules. The secondary processing step is believed to be slower than the primary processing step, which results in an intracellular pool of pre-rRNAs.

Pre-rRNAs have leader and tail sequences flanking the mature rRNA sequence. Leader and tail sequences are removed enzymatically (RNAse III cleavage) from the pre-rRNA during rRNA maturation and ribosome assembly to yield mature rRNA.

Pre-rRNAs are present at the beginning of rRNA transcript production. The production of mature ribosomes involves final processing of pre-rRNAs. Thus, the present invention provides benefits such as:

in growing bacterial cells, pre-rRNAs constitute a significant fraction of the total rRNA;
mature rRNA is stable in dormant and/or dead cells;
pre-rRNA sequences are not present in mature rRNA;
pre-rRNA sequences are phylogenetically specific (i.e., are not conserved); and
the method reduces the number of false positives with samples containing non-viable cells and mature RNA.

The EF-3 mRNA Assay

Several systems targeting pre-rRNA sequences in *C. albicans* were designed and evaluated with different treatments but did not clearly identify the best viability indicator.

Thus, other targets were considered for the specific *C. albicans* strain and a new system targeting the mRNA for the EF-3 gene has been selected.

The translation elongation factors for eubacteria and eukaryotes play a basic role in protein synthesis. These factors are a set of proteins that are used in protein synthesis in the growing cells. Translation elongation in eukaryotes is promoted by two factors: EF-1 and EF-2. However, yeast elongation requires a third factor: EF-3, which is a unique and essential requirement of the fungal translational apparatus. This gene is essential for the survival of yeast.

The EF-3 mRNA level increases rapidly upon dilution of a stationary culture into fresh medium, reaches it maximal level during the exponential growth phase, and declines to low levels during the transition and the stationary phase. Therefore, EF-3 expression is regulated during batch growth and can be related to cell growth rate. The present invention takes advantage of this characteristic as well.

Examples provided herein pertain to specific assays for compendia microbes requested in the PET guidelines (EP Chapter 5.1.3 and USP Chapter 51): *Escherichia coli* (*E. coli*) ATCC No. 8739, *Pseudomonas aeruginosa* (*P. aeruginosa*) ATCC No. 9027, *Staphylococcus aureus* (*S. aureus*) ATCC No. 6538, *Candida albicans* (*C. albicans*) ATCC No. 10231 and *Aspergillus brasiliensis* (*A. brasiliensis*) ATCC No. 16404, and for other relevant microbes for which viability assays are of interest: *Serratia marcescens* (*S. marcescens*), *Bacillus subtilis* (*B. subtilis*) and *Staphylococcus epidermidis* (*S. epidermidis*).

Assay Development Example One

*E. coli, B. subtilis* and *S. marcescens*

Figure 2:
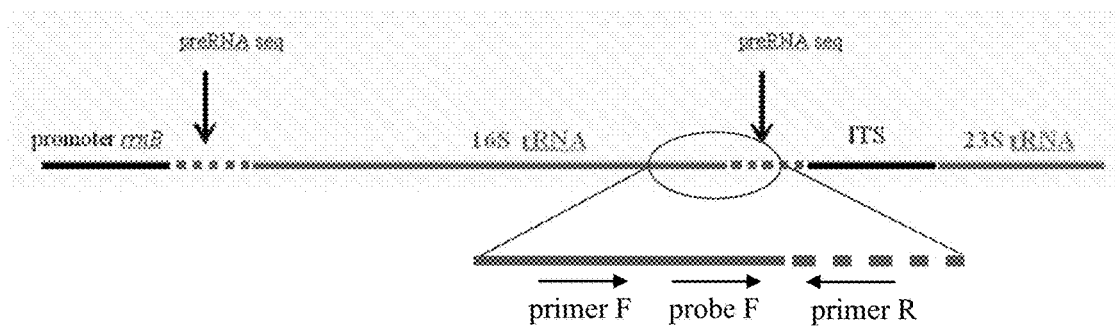
FIG. 2 illustrates design of *E. coli, B. subtilis* and *S. marcescens* pre-rRNA-specific systems.

The specific systems for *E. coli, B. subtilis* and *S. marcescens* are designed on the 3' end of the 16S rRNA transcript. The three systems are species-specific. In these examples, the reverse primer hybridizes on the pre-rRNA region and the forward primer and probe in the mature rRNA region. The amplification will therefore be effective only if pre-rRNAs are present in the cells. FIG. 2 illustrates *E. coli, B. subtilis* and *S. marcescens* pre-rRNA-specific systems designed in the 3' end of the 16S pre-rRNA for use with RT-PCR (forward primer, reverse primer, and forward probe).

Assay Development Example Two

*S. aureus, P. aeruginosa* and *S. epidermidis*

Figure 3:
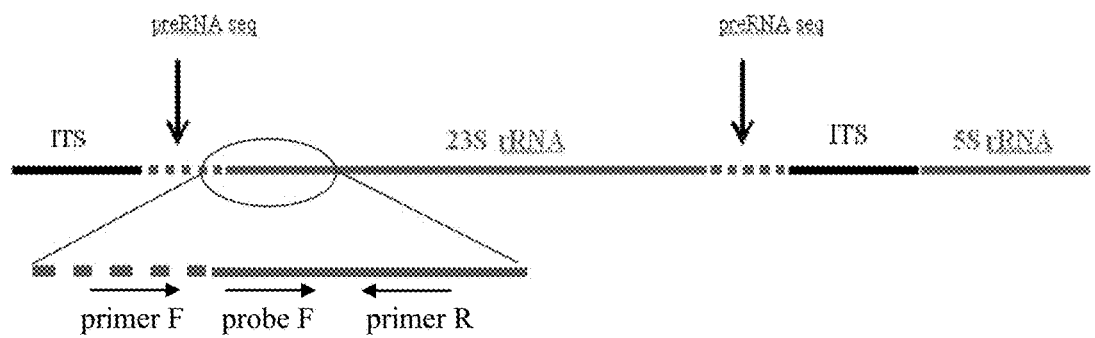
FIG. 3 illustrates design of *S. aureus, P. aeruginosa* and *S. epidermidis* pre-rRNA-specific systems.

The specific systems for *S. aureus, P. aeruginosa* and *S. epidermidis* are designed on the 5' end of the 23S rRNA. The three systems are species-specific. The forward primer hybridizes in the pre-rRNA region and the reverse primer and the forward probe in the mature rRNA region. The amplification is thus effective only if pre-rRNAs are present in the cells. FIG. 3 illustrates *S. aureus, P. aeruginosa* and *S. epidermidis* pre-rRNA-specific systems designed in the 5' end of the 23S pre-rRNA for use with RT-PCR (forward primer, reverse primer, and forward probe).

Assay Development Example Three

*A. brasiliensis*

Figure 4:
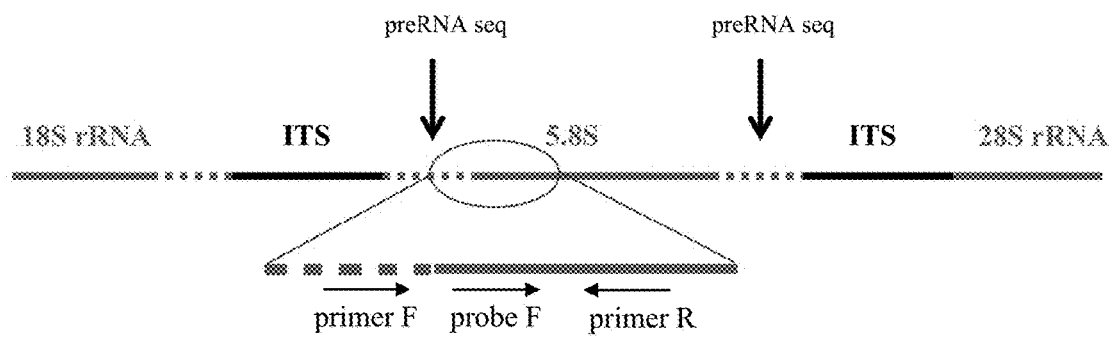
FIG. 4 illustrates design of *A. brasiliensis* pre-rRNA-specific system.

The specific system for *A. brasiliensis* is designed on the 5' end of the 5.8S rRNA. This system is species-specific. The forward primer hybridizes in the pre-rRNA region and the reverse primer and the forward probe in the mature rRNA region. The amplification is thus effective only if pre-rRNAs are present in the cells. FIG. 4 illustrates *A. brasiliensis* pre-rRNA-specific systems designed in the 5' end of the 5.8S pre-rRNA for use with RT-PCR (forward primer, reverse primer, and forward probe).

Assay Development Example Four

Specific EF-3 mRNA Assay for *C. albicans*

Figure 5:
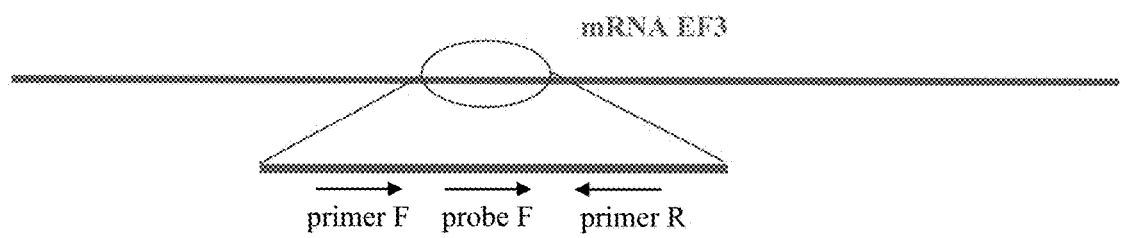
FIG. 5 illustrates design of *C. albicans* EF-3 mRNA-specific system.

The specific system for *C. albicans* is designed on the mRNA of the EF-3 gene. This system is species-specific. The forward primer, the forward probe and the reverse primer hybridize in the internal sequence of the mRNA of the EF-3 gene. The amplification is thus effective only if the EF-3 mRNAs are present in the cells. FIG. 5 illustrates *C. albicans* EF-3 mRNA specific system designed in the internal sequence of the EF-3 mRNA for use with RT-PCR (forward primer, reverse primer, and forward probe).

Protocol for Formulation Screening and/or Preservative Efficacy Testing (PET)

Assays such as those disclosed herein, and assays developed under the guidelines of the provided examples, can be used in Formulation Screening and/or Preservative Efficacy Testing. An exemplary protocol is as follows: non-treated (or viable) and preservative-treated cells are analyzed in parallel with the same procedure and the same reagents:

- Cells are calibrated to an expected density (CFU/ml) and collected by centrifugation on a filter membrane.
- Two milliliters of RNA Booster (nutrients) are applied to the membrane of the filtration unit and these are incubated two hours for bacteria and four hours for fungi at 35° C.±2° C. (or appropriate temperature).
- After incubation, the filtration units are centrifuged to remove the RNA Booster and 1.5 milliliters of lysis buffer are added to each membrane.
- Cell lysates are recovered manually by pipetting and transferred into a lysis tube for a mechanical lysis process.
- Lysate is then transferred in a sample prep tube.
- RNA is extracted and purified using a known nucleic acid isolation method (i.e., RNA magnetic beads, silica resin).
- DNA is removed by DNAse treatment to ensure predominantly an RNA target.
- Eluted RNA is amplified by RT-PCR. The master mix used for the RT-PCR contains all reagents needed for the RT-PCR including specific primers and probe targeting the pre-rRNA or EF-3 mRNA sequences.

The referenced guidelines followed for this assay are the European Pharmacopoeia (EP)—Chapter 5.1.3 <<Efficacy of Antimicrobial Preservation>> and the United States Pharmacopoeia (USP)—Chapter 51 <<Antimicrobial Effectiveness Testing>>. The value obtained by RT-PCR for the non-treated cells is compared to the value obtained for the treated cells. As used herein Ct stands for threshold cycle; i.e., the intersection between an amplification curve and a threshold line. According to the EP requirements, in a positive result as disclosed herein the difference of the Ct values is at least 3 logs, which corresponds to a ΔCt≥10 for bacteria and at least 2 logs, which corresponds to a ΔCt≥6.6 for fungi, after one day (24 hours) and seven days, respectively, for bacteria and fungi, of preservative treatment. USP requires data analysis after seven days and fourteen days for bacteria and fungi, respectively.

Experimental Data

The specific pre-rRNA assays disclosed herein are assessed with the following microbes: *E. coli*, *P. aeruginosa*, *S. aureus*, *S. marcescens*, *B. subtilis*, *S. epidermidis* and *A. brasiliensis*. Six different treatment methods are used: heat and isopropanol killing, preservative treatments with BAC (Benzalkonium Chloride), Poly-Q (PolyQuaternium) and IPBC (Iodopropynyl Butylcarbamate) and a commercial contact lens solution (which is formulated with other chemicals in addition to two preservatives (polyaminopropyl biguanide and polyquaternium)). The efficacy of these chemicals is assessed.

The specific EF-3 mRNA assay disclosed herein is assessed with *C. albicans* and four different treatment methods: heat killing, preservatives treatments with BAC (Benzalkonium Chloride) and IPBC (Iodopropynyl Butylcarbamate) and the commercial contact lens solution treatment.

Preservative treatments were evaluated at high cells concentrations ($10^6$ and $10^5$ cells per assay) that are commonly used for formulation screening. Five replicates at each cell concentration were analyzed. The Ct value corresponds to the RT-PCR cycle for which the level of fluorescence is outside the fluorescence background. The method compares Ct values for non-treated and treated cells and is expressed as the ΔCt.

The tables set forth below summarize the Ct values obtained for six bacteria and two fungi using six treatments: Heat, Isopropanol, Preservatives BAC, Poly-Q and IPBC and a commercial contact lens solution. Ct values obtained for non-treated cells (viable) are compared to Ct values obtained for treated cells. The ΔCt calculated is reported and must be ≥10 to meet the specification of 3 logs reduction for bacteria and must be ≥6.6 to meet the specification of 2 logs reduction for fungi. All assays are performed on the BD Max6 instrument from Becton Dickinson. Data are obtained by multiple operators on different days.

Heat Killing Treatment

TABLE 1

Results obtained with *Escherichia coli* and heat killing treatment (80° C. ± 2° C., 90 minutes):

| Samples | Ct Viable | Mean Ct | Ct Treated | Mean Ct | Δ Ct Viable – Dead |
|---|---|---|---|---|---|
| *E. coli* - Heat Killing - Operator 1 | | | | | |
| *E coli* $10^6$ cells | 10.38 | 10.76 | 29.91 | 31.53 | 20.78 |
| | 10.42 | | 29.92 | | |
| | 11.05 | | 31.80 | | |
| | 11.18 | | 34.79 | | |
| | 13.81 | | 31.26 | | |
| *E coli* $10^5$ cells | 13.86 | 13.91 | 31.50 | 31.58 | 17.68 |
| | 13.71 | | 32.09 | | |
| | 13.62 | | 31.46 | | |
| | 14.08 | | 31.37 | | |
| | 14.27 | | 31.49 | | |
| NC | 35.03 | 35.65 | 36.93 | 36.57 | |
| | 36.26 | | 36.21 | | |
| *E. coli* - Heat Killing - Operator 2 | | | | | |
| *E coli* $10^6$ cells | 25.39 | 11.39 | 32.42 | 31.68 | 20.29 |
| | 11.81 | | 32.61 | | |
| | 11.20 | | 31.45 | | |
| | 11.28 | | 31.12 | | |
| | 11.27 | | 30.81 | | |
| *E coli* $10^5$ cells | 13.77 | 13.66 | 30.56 | 30.93 | 17.26 |
| | 13.27 | | 31.60 | | |
| | 14.21 | | 30.83 | | |
| | 13.81 | | 31.07 | | |
| | 13.26 | | 30.58 | | |
| NC | 32.46 | 34.75 | 33.90 | 33.55 | |
| | 37.04 | | 33.20 | | |

NC = Negative Control - Control plate of treated cells ($10^6$ cells) shows no colony on plate.

TABLE 2

Results obtained with *Pseudomonas aeruginosa* and heat killing treatment (80° C. ± 2° C., 90 minutes):
*P. aeruginosa* - Heat Killing - Operator 1

| Samples | Ct Viable | Mean Ct | Ct Treated | Mean Ct | Δ Ct Viable – Dead |
|---|---|---|---|---|---|
| *P. aeruginosa* $10^6$ cells | 18.48 | 18.93 | 29.89 | 31.15 | 12.21 |
| | 18.92 | | 32.13 | | |
| | 18.41 | | 30.58 | | |
| | 20.34 | | 31.95 | | |
| | 18.52 | | 31.18 | | |
| *P. aeruginosa* $10^5$ cells | 21.10 | 21.58 | 33.35 | 32.97 | 11.39 |
| | 22.09 | | 33.66 | | |
| | 21.32 | | 32.06 | | |
| | 21.95 | | 32.80 | | |
| | 21.43 | | Negative | | |
| NC | Negative | Negative | Negative | 38.52 | |
| | | | 38.52 | | |

NC = Negative Control - Control plate of treated cells ($10^6$ cells) shows no colony on plate.

TABLE 3

Results obtained with *Staphylococcus aureus* and heat killing treatment (80° C. ± 2° C., 90 minutes):
*S. aureus* - Heat Killing - Operator 1

| Samples | Ct Viable | Mean Ct | Ct Treated | Mean Ct | Δ Ct Viable – Dead |
|---|---|---|---|---|---|
| *S. aureus* $10^6$ cells | 12.65 | 12.67 | 26.90 | 26.14 | 13.47 |
| | 12.69 | | 26.19 | | |
| | 12.68 | | 26.16 | | |
| | 12.69 | | 26.03 | | |
| | 12.65 | | 25.42 | | |
| *S. aureus* $10^5$ cells | 16.88 | 16.96 | 29.10 | 29.29 | 12.33 |
| | 17.05 | | 29.61 | | |
| | 16.94 | | 28.33 | | |
| | 17.10 | | 29.84 | | |
| | 16.85 | | 29.57 | | |
| NC | Negative | 39.73 | 38.18 | 38.18 | |
| | 39.73 | | Negative | | |

NC = Negative Control - Control plate of treated cells ($10^6$ cells) shows no colony on plate.

TABLE 4

Results obtained with *Serratia marcescens* and heat killing treatment (80° C. ± 2° C., 90 minutes):
*S. marcescens* - Heat Killing

| Samples | Ct Viable | Mean Ct | Ct Treated | Mean Ct | Δ Ct Viable – Dead |
|---|---|---|---|---|---|
| *S. marcescens* $10^6$ cells | 13.40 | 12.88 | 31.40 | 30.96 | 18.08 |
| | 12.80 | | 31.30 | | |
| | 12.40 | | 31.60 | | |
| | 13.10 | | 31.00 | | |
| | 12.70 | | 29.50 | | |
| *S. marcescens* $10^5$ cells | 17.50 | 17.00 | 31.70 | 31.36 | 14.36 |
| | 16.00 | | 31.70 | | |
| | 15.90 | | 30.70 | | |
| | 18.90 | | 32.00 | | |
| | 16.70 | | 30.70 | | |
| NC | Negative | Negative | Negative | 39.40 | |
| | Negative | | 39.40 | | |

NC = Negative Control - Control plate of treated cells ($10^6$ cells) shows no colony on plate.

TABLE 5

Results obtained with *Bacillus subtilis* and heat killing treatment (80° C. ± 2° C., 90 minutes):
*B. subtilis* - Heat Killing - Operator 1

| Samples | Ct Viable | Mean Ct | Ct Treated | Mean Ct | Δ Ct Viable – Dead |
|---|---|---|---|---|---|
| *B. subtilis* $10^6$ cells | 15.79 | 17.54 | 28.00 | 28.92 | 11.38 |
| | 17.44 | | 29.61 | | |
| | 15.94 | | 30.27 | | |
| | 19.20 | | 28.82 | | |
| | 19.33 | | 27.90 | | |
| *B. subtilis* $10^5$ cells | 19.23 | 18.78 | 31.56 | 31.48 | 12.70 |
| | 18.90 | | 31.67 | | |
| | 19.85 | | 31.20 | | |
| | 18.16 | | 31.73 | | |
| | 17.78 | | 31.26 | | |
| NC | Negative | Negative | Negative | Negative | |
| | Negative | | Negative | | |

NC = Negative Control - Control plate of treated cells ($10^6$ cells) shows no colony on plate.

TABLE 6

Results obtained with *Staphylocuccus epidermidis* and heat killing treatment (80° C. ± 2° C., 90 minutes):
*S. epidermidis* - Heat Killing

| Samples | Ct Viable | Mean Ct | Ct Treated | Mean Ct | Δ Ct Viable – Dead |
|---|---|---|---|---|---|
| *S. epidermidis* $10^6$ cells | 16.48 | 16.61 | 28.67 | 28.11 | 11.50 |
| | 16.64 | | 27.97 | | |
| | 16.90 | | 27.91 | | |
| | 16.89 | | 28.20 | | |
| | 16.17 | | 27.81 | | |
| *S. epidermidis* $10^5$ cells | 21.73 | 21.16 | 30.66 | 31.19 | 10.03 |
| | 21.05 | | 31.57 | | |
| | 20.64 | | 31.35 | | |
| | 21.13 | | 31.14 | | |
| | 21.23 | | 31.21 | | |
| NC | Negative | Negative | Negative | Negative | |
| | Negative | | Negative | | |

NC = Negative Control - Control plate of treated cells ($10^6$ cells) shows no colony on plate.

TABLE 7

Results obtained with *Candida albicans* and heat killing treatment (80° C. ± 2° C., 90 minutes):
*C. albicans* - Heat Killing

| Samples | Ct Viable | Mean Ct | Ct Treated | Mean Ct | Δ Ct Viable – Dead |
|---|---|---|---|---|---|
| *C. albicans* $10^5$ cells | 17.60 | 17.82 | 28.10 | 27.94 | 10.12 |
| | 18.00 | | 28.00 | | |
| | 18.00 | | 28.20 | | |
| | 17.40 | | 27.80 | | |
| | 18.10 | | 27.60 | | |
| NC | Negative | | Negative | | |

NC = Negative Control - Control plate of treated cells ($10^5$ cells) shows no colony on plate.

Isopropanol Treatment

TABLE 8

Results obtained with *Escherichia coli* and Isopropanol treatment (1 H at room temperature):
*E. coli* - Isopropanol Killing - Operator 2

| Samples | Ct Viable | Mean Ct | Ct Treated | Mean Ct | Δ Ct Viable − Dead |
|---|---|---|---|---|---|
| *E coli* $10^6$ cells | 11.81 | 11.93 | 32.98 | 32.93 | 21.00 |
|  | 12.10 |  | 33.93 |  |  |
|  | 11.52 |  | 32.91 |  |  |
|  | 11.99 |  | 32.51 |  |  |
|  | 12.21 |  | 32.31 |  |  |
| *E coli* $10^5$ cells | 14.67 | 14.88 | 33.02 | 32.44 | 17.56 |
|  | 14.64 |  | 33.36 |  |  |
|  | 15.34 |  | 32.52 |  |  |
|  | 15.26 |  | 31.38 |  |  |
|  | 14.50 |  | 31.93 |  |  |
| NC | 35.41 | 34.12 | 34.52 | 34.61 |  |
|  | 32.83 |  | 34.71 |  |  |

NC = Negative Control - Control plate of treated cells ($10^6$ cells) shows no colony on plate.

TABLE 9

Results obtained with *Pseudomonas aeruginosa* and Isopropanol treatment (1 H at room temperature):
*P. aeruginosa* - Isopropanol Killing - Operator 1

| Samples | Ct Viable | Mean Ct | Ct Treated | Mean Ct | Δ Ct Viable − Dead |
|---|---|---|---|---|---|
| *P. aeruginosa* $10^6$ cells | 19.91 | 20.25 | 34.18 | 33.70 | 13.45 |
|  | 19.51 |  | 33.26 |  |  |
|  | 21.25 |  | 34.59 |  |  |
|  | 19.63 |  | 33.28 |  |  |
|  | 20.97 |  | 33.21 |  |  |
| *P. aeruginosa* $10^5$ cells | 23.17 | 24.31 | 34.62 | 35.31 | 10.99 |
|  | 23.83 |  | 34.83 |  |  |
|  | 23.23 |  | 34.29 |  |  |
|  | 26.43 |  | 33.99 |  |  |
|  | 24.90 |  | 38.81 |  |  |
| NC | Negative | Negative | Negative | Negative |  |
|  | Negative |  | Negative |  |  |

NC = Negative Control - Control plate of treated cells ($10^6$ cells) shows no colony on plate.

TABLE 10

Results obtained with *Staphylococcus aureus* and Isopropanol treatment (1 H at room temperature):
*S. aureus* - Isopropanol Killing - Operator 1

| Samples | Ct Viable | Mean Ct | Ct Treated | Mean Ct | Δ Ct Viable − Dead |
|---|---|---|---|---|---|
| *S. aureus* $10^6$ cells | 23.71 | 12.81 | 24.94 | 25.90 | 13.09 |
|  | 12.87 |  | 26.57 |  |  |
|  | 12.62 |  | 26.32 |  |  |
|  | 12.77 |  | 26.40 |  |  |
|  | 12.99 |  | 25.27 |  |  |
| *S. aureus* $10^5$ cells | 16.67 | 16.88 | 29.99 | 29.68 | 12.80 |
|  | 17.17 |  | 29.43 |  |  |
|  | 16.62 |  | 29.12 |  |  |
|  | 16.76 |  | 29.97 |  |  |
|  | 17.17 |  | 29.89 |  |  |
| NC | Negative | 24.20 | Negative | Negative |  |
|  | 24.20 |  | Negative |  |  |

NC = Negative Control - Control plate of treated cells ($10^6$ cells) shows no colony on plate.

TABLE 11

Results obtained with *Serratia marcescens* and Isopropanol treatment (1 H at room temperature):
*S. marcescens* - Isopropanol Killing

| Samples | Ct Viable | Mean Ct | Ct Treated | Mean Ct | Δ Ct Viable − Dead |
|---|---|---|---|---|---|
| *S. marcescens* $10^6$ cells | 12.00 | 12.80 | 25.40 | 25.98 | 13.18 |
|  | 12.40 |  | 25.50 |  |  |
|  | 13.20 |  | 26.90 |  |  |
|  | 13.10 |  | 26.20 |  |  |
|  | 13.30 |  | 25.90 |  |  |
| *S. marcescens* $10^5$ cells | 18.10 | 17.00 | 29.10 | 30.20 | 13.20 |
|  | 16.50 |  | 30.70 |  |  |
|  | 18.10 |  | 31.00 |  |  |
|  | 16.40 |  | 29.90 |  |  |
|  | 15.90 |  | 30.30 |  |  |
| NC | 36.60 | 37.45 | Negative | Negative |  |
|  | 38.30 |  | Negative |  |  |

NC = Negative Control - Control plate of treated cells ($10^6$ cells) shows no colony on plate.

Preservative BAC Treatment

TABLE 12

Results obtained with *Escherichia coli* and preservative BAC treatment (24 H at room temperature):
*E. coli* - BAC Preservative Killing - Operator 2

| Samples | Ct Viable | Mean Ct | Ct Treated | Mean Ct | Δ Ct Viable − Dead |
|---|---|---|---|---|---|
| *E. coli* $10^6$ cells | 11.60 | 11.56 | 30.48 | 32.90 | 21.33 |
|  | 11.33 |  | 33.39 |  |  |
|  | 11.30 |  | 32.61 |  |  |
|  | 10.85 |  | 34.26 |  |  |
|  | 12.73 |  | 33.74 |  |  |
| *E. coli* $10^5$ cells | 13.40 | 13.67 | 32.65 | 32.23 | 18.57 |
|  | 13.81 |  | 31.54 |  |  |
|  | 13.37 |  | 31.77 |  |  |
|  | 14.23 |  | 32.76 |  |  |
|  | 13.53 |  | 32.45 |  |  |
| NC | 34.98 | 35.06 | 31.94 | 32.35 |  |
|  | 35.14 |  | 32.76 |  |  |

NC = Negative Control - Control plate of treated cells ($10^6$ cells) shows no colony on plate.

TABLE 13

Results obtained with *Pseudomonas aeruginosa* and preservative BAC treatment (24 H at room temperature):
*P. aeruginosa* - BAC Preservative Killing - Operator 1

| Samples | Ct Viable | Mean Ct | Ct Treated | Mean Ct | Δ Ct Viable − Dead |
|---|---|---|---|---|---|
| *P. aeruginosa* $10^6$ cells | 16.10 | 16.19 | 27.96 | 30.72 | 14.53 |
|  | 16.39 |  | Negative |  |  |
|  | 16.65 |  | Negative |  |  |
|  | 15.56 |  | Negative |  |  |
|  | 16.24 |  | 33.48 |  |  |
| *P. aeruginosa* $10^5$ cells | 19.53 | 19.53 | Negative | 31.92 | 12.39 |
|  | 20.04 |  | Negative |  |  |
|  | 19.47 |  | 31.09 |  |  |
|  | 19.43 |  | 33.12 |  |  |
|  | 19.18 |  | 31.55 |  |  |

TABLE 13-continued

Results obtained with *Pseudomonas aeruginosa* and preservative
BAC treatment (24 H at room temperature):
*P. aeruginosa* - BAC Preservative Killing - Operator 1

| Samples | Ct Viable | Mean Ct | Ct Treated | Mean Ct | Δ Ct Viable – Dead |
|---|---|---|---|---|---|
| NC | Negative | Negative | Negative | Negative | |
| | Negative | | Negative | | |

NC = Negative Control - Control plate of treated cells ($10^6$ cells) shows no colony on plate.

TABLE 14

Results obtained with *Staphylococcus aureus* and preservative
BAC treatment (24 H at room temperature):
*S. aureus* - BAC Preservative Killing - Operator 2

| Samples | Ct Viable | Mean Ct | Ct Treated | Mean Ct | Δ Ct Viable – Dead |
|---|---|---|---|---|---|
| *S. aureus* $10^6$ cells | 13.91 | 14.07 | 26.71 | 26.72 | 12.65 |
| | 13.96 | | 26.64 | | |
| | 14.09 | | 26.23 | | |
| | 14.25 | | 27.50 | | |
| | 14.15 | | 26.54 | | |
| *S. aureus* $10^5$ cells | 17.53 | 17.45 | 29.75 | 29.73 | 12.29 |
| | 17.88 | | 30.23 | | |
| | 17.23 | | 29.39 | | |
| | 17.30 | | 29.28 | | |
| | 17.30 | | 30.03 | | |
| NC | Negative | Negative | 37.75 | 37.83 | |
| | Negative | | 37.91 | | |

NC = Negative Control - Control plate of treated cells ($10^6$ cells) shows no colony on plate.

TABLE 15

Results obtained with *Serratia marcescens* and preservative
BAC treatment (24 H at room temperature):
*S. marcescens* - BAC Preservative Killing

| Samples | Ct Viable | Mean Ct | Ct Treated | Mean Ct | Δ Ct Viable – Dead |
|---|---|---|---|---|---|
| *S. marcescens* $10^6$ cells | 11.60 | 11.93 | 32.80 | 34.20 | 22.28 |
| | 12.10 | | 35.50 | | |
| | 12.30 | | 34.20 | | |
| | 11.70 | | 34.30 | | |
| *S. marcescens* $10^5$ cells | 15.30 | 16.04 | Negative | 36.13 | 20.09 |
| | 15.20 | | Negative | | |
| | 15.80 | | 36.40 | | |
| | 16.10 | | 35.30 | | |
| | 17.80 | | 36.70 | | |
| NC | Negative | Negative | Negative | Negative | |
| | Negative | | Negative | | |

NC = Negative Control - Control plate of treated cells ($10^6$ cells) shows no colony on plate.

TABLE 16

Results obtained with *Aspergillus brasiliensis* and preservative BAC
treatment (from day 1 to day 7 at room temperature)
*A. brasiliensis* - BAC Preservative Treatment

| | Samples | Ct Viable | Mean Ct | Ct Treated | Mean Ct | Δ Ct Viable – Dead |
|---|---|---|---|---|---|---|
| Day 1 | *A. brasiliensis* $10^6$ cells | 10.00 | 10.20 | 22.10 | 21.83 | 11.63 |
| | | 10.60 | | 21.80 | | |
| | | 10.00 | | 21.60 | | |
| Day 2 | *A. brasiliensis* $10^6$ cells | 10.00 | 10.20 | 22.40 | 22.73 | 12.53 |
| | | 10.60 | | 21.90 | | |
| | | 10.00 | | 23.90 | | |
| Day 7 | *A. brasiliensis* $10^6$ cells | 10.00 | 10.20 | 22.60 | 23.27 | 13.07 |
| | | 10.60 | | 24.70 | | |
| | | 10.00 | | 22.50 | | |
| NC | | Negative | | Negative | | |

NC = Negative Control - Control plate of treated cells ($10^6$ cells) shows no colony on plate.

TABLE 17

Results obtained with *Candida albicans* and preservative BAC
treatment (from day 1 to day 14 at room temperature)
*C. albicans* - BAC Preservative Treatment

| | Samples | Ct Viable | Mean Ct | Ct Treated | Mean Ct | Δ Ct Viable – Dead |
|---|---|---|---|---|---|---|
| Day 1 | *C. albicans* $10^5$ cells | 18.30 | 18.10 | 29.30 | 32.00 | 13.90 |
| | | 17.80 | | 33.70 | | |
| | | 18.10 | | 32.70 | | |
| | | 18.10 | | 31.60 | | |
| | | 18.20 | | 32.70 | | |
| Day 7 | *C. albicans* $10^5$ cells | 18.30 | 18.10 | Negative | 33.67 | 15.57 |
| | | 17.80 | | 34.60 | | |
| | | 18.10 | | 34.10 | | |
| | | 18.10 | | 32.30 | | |
| | | 18.20 | | Negative | | |
| Day 14 | *C. albicans* $10^5$ cells | 18.30 | 18.10 | Negative | 32.23 | 14.13 |
| | | 17.80 | | 31.60 | | |
| | | 18.10 | | 32.70 | | |
| | | 18.10 | | 32.00 | | |
| | | 18.20 | | 32.60 | | |
| NC | | Negative | | Negative | | |

NC = Negative Control - Control plate of treated cells ($10^5$ cells) shows no colony on plate.

Preservative Poly-Q Treatment

TABLE 18

Results obtained with *Escherichia coli* and preservative
Poly-Q treatment (24 H at room temperature):
*E. coli* - Poly-Q Preservative Killing - Operator 2

| Samples | Ct Viable | Mean Ct | Ct Treated | Mean Ct | Δ Ct Viable – Dead |
|---|---|---|---|---|---|
| *E. coli* $10^6$ cells | 11.60 | 11.56 | error mix | 20.19 | 8.62 |
| | 11.33 | | 21.55 | | |
| | 11.30 | | 19.31 | | |
| | 10.85 | | 18.30 | | |
| | 12.73 | | 21.58 | | |
| *E. coli* $10^5$ cells | 13.40 | 13.67 | 23.28 | 26.59 | 12.92 |
| | 13.81 | | 22.62 | | |
| | 13.37 | | 30.10 | | |
| | 14.23 | | 32.51 | | |
| | 13.53 | | 24.43 | | |

TABLE 18-continued

Results obtained with *Escherichia coli* and preservative
Poly-Q treatment (24 H at room temperature):
*E. coli* - Poly-Q Preservative Killing - Operator 2

| Samples | Ct Viable | Mean Ct | Ct Treated | Mean Ct | Δ Ct Viable – Dead |
|---|---|---|---|---|---|
| NC | 34.98 | 35.06 | 31.00 | 31.80 | |
|    | 35.14 |       | 32.59 |       | |

NC = Negative Control - Control plate of treated cells ($10^6$ cells) shows large amount of colonies on plate (>300). Treatment is not efficient at 100%.

TABLE 19

Results obtained with *Pseudomonas aeruginosa* and preservative
Poly-Q treatment (24 H at room temperature):
*P. aeruginosa* - Poly-Q Preservative Killing - Operator 1

| Samples | Ct Viable | Mean Ct | Ct Treated | Mean Ct | Δ Ct Viable – Dead |
|---|---|---|---|---|---|
| *P. aeruginosa* $10^6$ cells | 16.10 | 16.19 | 24.35 | 24.34 | 8.15 |
|  | 16.39 |  | 25.62 |  |  |
|  | 16.65 |  | 24.41 |  |  |
|  | 15.56 |  | 24.07 |  |  |
|  | 16.24 |  | 23.22 |  |  |
| *P. aeruginosa* $10^5$ cells | 19.53 | 19.53 | 26.65 | 27.19 | 7.66 |
|  | 20.04 |  | 28.11 |  |  |
|  | 19.47 |  | 27.65 |  |  |
|  | 19.43 |  | 27.45 |  |  |
|  | 19.18 |  | 26.10 |  |  |
| NC | Negative | Negative | Negative | Negative | |
|  | Negative |  | Negative |  | |

NC = Negative Control - Control plate of treated cells ($10^6$ cells) shows no colony on plate.

TABLE 20

Results obtained with *Staphylococcus aureus* and preservative
Poly-Q treatment (24 H at room temperature):
*S. aureus* - Poly-Q Preservative Killing - Operator 1

| Samples | Ct Viable | Mean Ct | Ct Treated | Mean Ct | Δ Ct Viable – Dead |
|---|---|---|---|---|---|
| *S. aureus* $10^6$ cells | 13.46 | 12.89 | 22.99 | 22.94 | 10.05 |
|  | 12.82 |  | 23.06 |  |  |
|  | 12.67 |  | 21.45 |  |  |
|  | 12.61 |  | 23.01 |  |  |
|  | 12.89 |  | 24.19 |  |  |
| *S. aureus* $10^5$ cells | 16.07 | 16.34 | 24.39 | 26.02 | 9.68 |
|  | 16.77 |  | 26.08 |  |  |
|  | 16.14 |  | 26.47 |  |  |
|  | 16.27 |  | 26.39 |  |  |
|  | 16.46 |  | 26.76 |  |  |
| NC | Negative | 36.29 | Negative | Negative | |
|  | 36.29 |  | Negative |  |  |

NC = Negative Control - Control plate of treated cells ($10^6$ cells) shows few colonies on plate (30). Treatment is not efficient at 100%.

TABLE 21

Results obtained with *Serratia marcescens* and preservative
Poly-Q treatment (24 H at room temperature):
*S. marcescens* - Poly-Q Preservative Killing

| Samples | Ct Viable | Mean Ct | Ct Treated | Mean Ct | Δ Ct Viable – Dead |
|---|---|---|---|---|---|
| *S. marcescens* $10^6$ cells | 11.60 | 11.93 | 21.40 | 22.48 | 10.55 |
|  | 12.10 |  | 24.50 |  |  |

TABLE 21-continued

Results obtained with *Serratia marcescens* and preservative
Poly-Q treatment (24 H at room temperature):
*S. marcescens* - Poly-Q Preservative Killing

| Samples | Ct Viable | Mean Ct | Ct Treated | Mean Ct | Δ Ct Viable – Dead |
|---|---|---|---|---|---|
|  | 12.30 |  | 22.90 |  |  |
|  | 11.70 |  | 21.10 |  |  |
| *S. marcescens* $10^5$ cells | 15.30 | 16.04 | 31.20 | 29.50 | 13.46 |
|  | 15.20 |  | 25.40 |  |  |
|  | 15.80 |  | 29.40 |  |  |
|  | 16.10 |  | 33.00 |  |  |
|  | 17.80 |  | 28.50 |  |  |
| NC | Negative | Negative | Negative | Negative | |
|  | Negative |  | Negative |  |  |

NC = Negative Control - Control plate of treated cells ($10^6$ cells) shows colonies on plate (>300). Treatment is not efficient at 100%.

Preservative IPBC Treatment

TABLE 22

Results obtained with *Aspergillus brasiliensis* and preservative IPBC
treatment (from day 1 to day 7 at room temperature):

*A. brasiliensis* - IPBC Preservative Treatment

| Samples | | Ct Viable | Mean Ct | Ct Treated | Mean Ct | Δ Ct Viable – Dead |
|---|---|---|---|---|---|---|
| Day 1 | *A. brasiliensis* $10^6$ cells | 11.00 | 10.98 | 15.20 | 15.48 | 4.50 |
|  |  | 11.20 |  | 15.20 |  |  |
|  |  | 10.80 |  | 15.20 |  |  |
|  |  | 10.50 |  | 15.80 |  |  |
|  |  | 11.40 |  | 16.00 |  |  |
| Day 2 | *A. brasiliensis* $10^6$ cells | 11.00 | 10.98 | 26.30 | 25.22 | 14.24 |
|  |  | 11.20 |  | 23.80 |  |  |
|  |  | 10.80 |  | 24.60 |  |  |
|  |  | 10.50 |  | 24.30 |  |  |
|  |  | 11.40 |  | 27.10 |  |  |
| Day 7 | *A. brasiliensis* $10^6$ cells | 11.00 | 10.98 | 24.80 | 23.72 | 12.74 |
|  |  | 11.20 |  | 23.50 |  |  |
|  |  | 10.80 |  | 23.10 |  |  |
|  |  | 10.50 |  | 22.70 |  |  |
|  |  | 11.40 |  | 24.50 |  |  |
| NC | | Negative |  | Negative |  |  |

NC = Negative Control - Control plate of treated cells ($10^6$ cells) shows colonies on plate (>300) at day 1, and no colony at day 2 and day 7.

TABLE 23

Results obtained with *Candida albicans* and preservative IPBC
treatment (from day 1 to day 14 at room temperature):

*C. albicans* - IPBC Preservative Treatment

| Samples | | Ct Viable | Mean Ct | Ct Treated | Mean Ct | Δ Ct Viable – Dead |
|---|---|---|---|---|---|---|
| Day 1 | *C. albicans* $10^5$ cells | 18.30 | 18.10 | 29.00 | 29.70 | 11.60 |
|  |  | 17.80 |  | 28.40 |  |  |
|  |  | 18.10 |  | 33.30 |  |  |
|  |  | 18.10 |  | 29.40 |  |  |
|  |  | 18.20 |  | 28.40 |  |  |
| Day 7 | *C. albicans* $10^5$ cells | 18.30 | 18.10 | 32.30 | 32.70 | 14.60 |
|  |  | 17.80 |  | 32.80 |  |  |
|  |  | 18.10 |  | 32.80 |  |  |
|  |  | 18.10 |  | 32.80 |  |  |
|  |  | 18.20 |  | 32.80 |  |  |
| Day 14 | *C. albicans* $10^5$ cells | 18.30 | 18.10 | Negative | 36.43 | 18.33 |
|  |  | 17.80 |  | 37.00 |  |  |
|  |  | 18.10 |  | 36.60 |  |  |

TABLE 23-continued

Results obtained with *Candida albicans* and preservative IPBC treatment (from day 1 to day 14 at room temperature):

*C. albicans* - IPBC Preservative Treatment

| Samples | Ct Viable | Mean Ct | Ct Treated | Mean Ct | Δ Ct Viable − Dead |
|---|---|---|---|---|---|
| | | 18.10 | | 35.30 | |
| | | 18.20 | | 36.80 | |
| NC | Negative | | Negative | | |

NC = Negative Control - Control plate of treated cells ($10^5$ cells) shows colonies on plate (>300) at day 1, and no colony at day 7 and day 14.

Commercial Contact Lens Solution Treatment

TABLE 24

Results obtained with *Escherichia coli* and a commercial contact lens solution treatment (24 H at room temperature):
*E. coli* - Contact lens commercial solution

| Samples | Ct Viable | Mean Ct | Ct Treated | Mean Ct | Δ Ct Viable − Dead |
|---|---|---|---|---|---|
| *E. coli* | 12.90 | 13.72 | 32.20 | 29.80 | 16.08 |
| $10^6$ cells | 13.80 | | 30.80 | | |
| | 13.50 | | 31.50 | | |
| | 15.00 | | 26.90 | | |
| | 13.40 | | 27.60 | | |
| *E. coli* | 15.90 | 16.28 | 32.20 | 31.73 | 15.45 |
| $10^5$ cells | 17.40 | | 34.00 | | |
| | 15.70 | | 31.90 | | |
| | 16.90 | | 28.80 | | |
| | 15.50 | | NT | | |
| NC | 36.10 | 34.55 | 32.40 | 33.20 | |
| | 33.00 | | 34.00 | | |

NC = Negative Control - Control plate of treated cells ($10^6$ cells) shows no colony on plate.

TABLE 25

Results obtained with *Serratia marcescens* and a commercial contact lens solution treatment (24 H at room temperature):
*S. marcescens* - Contact lens commercial solution

| Samples | Ct Viable | Mean Ct | Ct Treated | Mean Ct | Δ Ct Viable − Dead |
|---|---|---|---|---|---|
| *S. marcescens* | 12.90 | 12.70 | 28.80 | 27.94 | 15.24 |
| $10^6$ cells | 12.20 | | 27.80 | | |
| | 12.70 | | 27.70 | | |
| | 12.30 | | 27.80 | | |
| | 13.40 | | 27.60 | | |
| *S. marcescens* | 17.60 | 16.70 | 33.20 | 32.56 | 15.86 |
| $10^5$ cells | 16.90 | | 31.70 | | |
| | 16.20 | | 33.90 | | |
| | 17.00 | | 31.30 | | |
| | 15.80 | | 32.70 | | |
| NC | 38.30 | 38.35 | Negative | 38.80 | |
| | 38.40 | | Negative | | |

NC = Negative Control - Control plate of treated cells ($10^6$ cells) shows no colony on plate.

TABLE 26

Results obtained with *Candida albicans* and a commercial contact lens solution treatment (from day 1 to day 7 at room temperature):
*C. albicans* - Contact lens commercial solution

| Samples | Ct Viable | Mean Ct | Ct Treated | Mean Ct | Δ Ct Viable − Dead |
|---|---|---|---|---|---|
| Day 1 *C. albicans* $10^5$ cells | 17.10 | 17.32 | 32.20 | 30.26 | 12.94 |
| | 17.20 | | 32.90 | | |
| | 17.70 | | 29.90 | | |
| | 17.60 | | 28.00 | | |
| | 17.10 | | 28.30 | | |
| Day 7 *C. albicans* $10^5$ cells | 17.10 | 17.32 | 35.10 | 31.16 | 13.84 |
| | 17.20 | | 31.10 | | |
| | 17.70 | | 30.30 | | |
| | 17.50 | | 29.70 | | |
| | 17.10 | | 29.60 | | |
| NC | Negative | Negative | Negative | Negative | |

NC = Negative Control - Control plate of treated cells ($10^5$ cells) shows no colony on plate.

Preservative Screening Application

Figure 6:
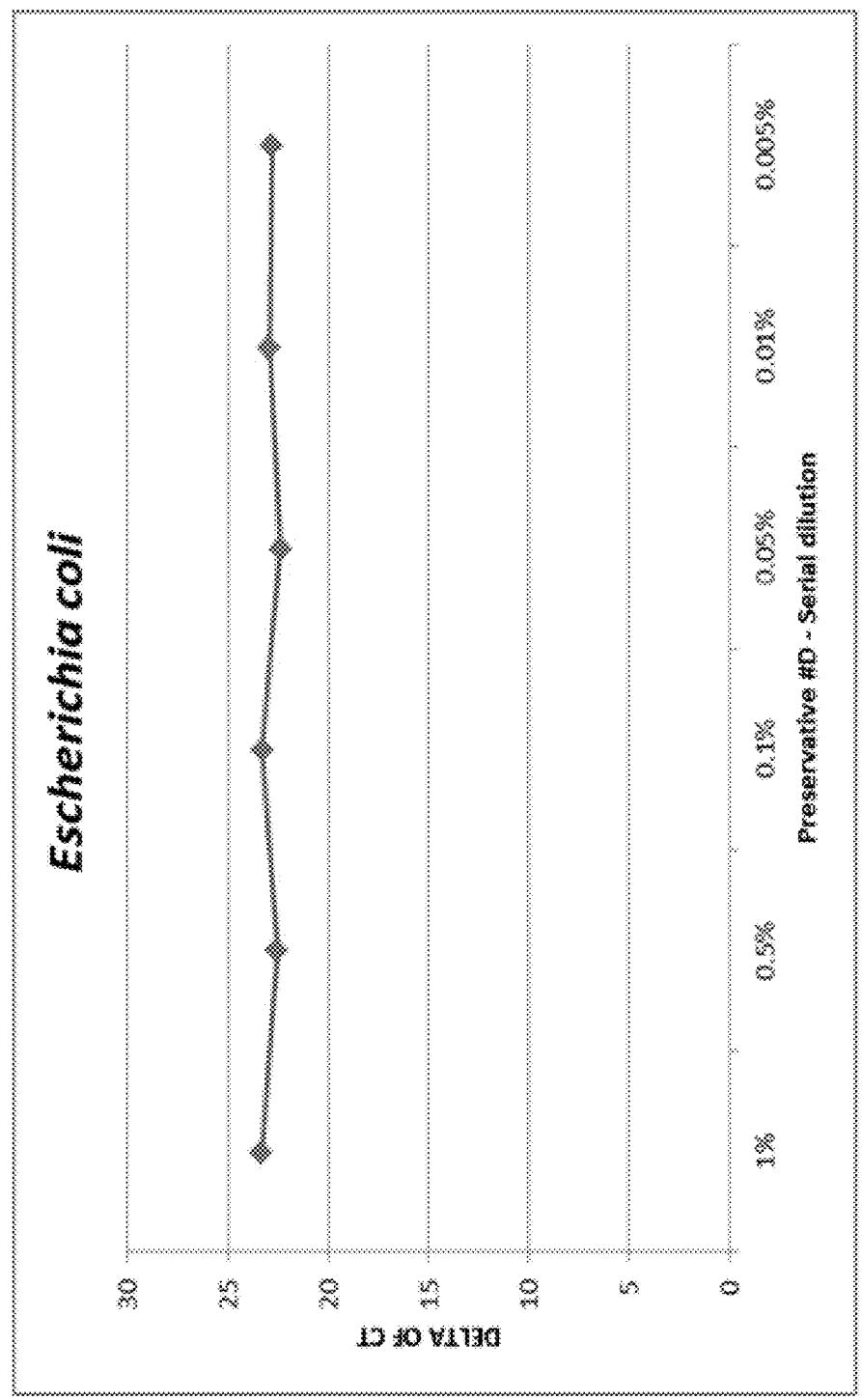
FIG. 6 illustrates results obtained with *Escherichia coli* and a preservative screening application.
Figure 7:
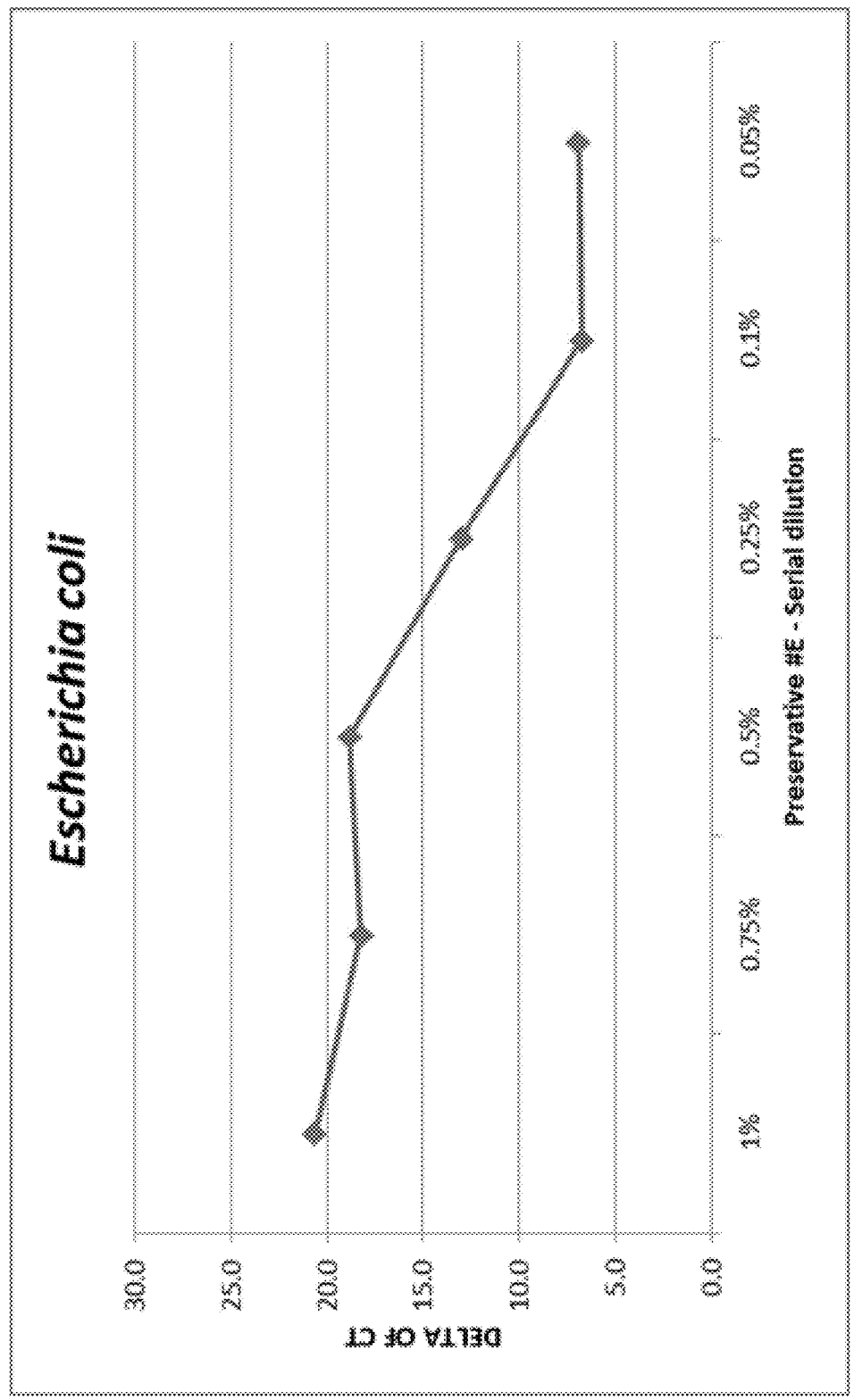
FIG. 7 illustrates results obtained with *Escherichia coli* and a preservative screening application.

FIG. 6 and FIG. 7 illustrate results obtained with *Escherichia coli* and a preservative screening application.

As shown in FIG. 6, this preservative D is effective from 1% to 0.005%. Control plate of treated cells ($10^6$ cells) shows no colony on plate for all preservative dilutions.

As shown in FIG. 7, this preservative E is ineffective at low concentrations. Control plate of treated cells ($10^6$ cells) shows colonies on plate (>300) for 0.25%, 0.1% and 0.05%, As illustrated herein, the time to result using the method and kit of the present invention is significantly decreased. Pre-rRNA and EF-3 mRNA assays are performed in two days (depending on the length of preservative treatment), while conventional methods require five days or more depending on the growth rates of the selected organism.

Moreover, viable but non-cultivable cells are detected by RT-PCR, but not by conventional growth-based methods thus reducing the number of false negatives. Furthermore, experimental data show that targeting pre-rRNA and EF-3 mRNA using a RT-PCR system is a useful tool for distinguishing viable (non-treated) from non-viable (treated) cells.

The technical problems observed with RT-PCR assays targeting mature rRNA sequences are addressed using this system. A ΔCt of four to five was obtained using the mature rRNA sequences (data not shown) while a ΔCt≥10 was obtained using the pre-rRNA systems.

The Poly-Q treatment did not show an efficient killing as control plates post-treatment still show bacteria growth, and so the ΔCt are significantly lower especially for *E. coli* and *P. aeruginosa*.

Overall, based on all data obtained to date, selected pre-rRNA and mRNA designed systems are species-specific and can be used for formulation screening and Preservative Efficacy Testing in filterable matrix.

New optimized protocols can be assessed in case of PCR interference due to inhibitors coming from the tested matrix. These optimizations can include new treatments or wash steps of the filter membrane.

Contemplated assays include an Internal Process Control (IPC) that ensures efficiency of the pre-rRNA and mRNA extraction and amplification process.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, since numerous modifications will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for identifying and quantifying viable microbial cells in one or more samples containing a microorganism of interest, comprising:
    (a) amplification of species-specific DNA from pre-rRNA-containing samples using a reverse transcription-polymerase chain reaction, said amplification step comprising:
        using a first primer complementary to a pre-rRNA region of said microorganism of interest;
        using a second primer complementary to a mature rRNA region of said microorganism of interest; and
        performing multiple cycles of amplification using said first primer and said second primer to yield detectable levels of amplified species-specific DNA; and
    (b) quantitation of said amplified species-specific DNA, said quantitation step comprising:
        using a fluorescently labeled hybridizing probe complementary to said mature rRNA region of said microorganism of interest;
        using said first primer complementary to said pre-rRNA region of said microorganism of interest;
        using said second primer complementary to said mature rRNA region of said microorganism of interest; and
        performing multiple cycles of amplification using said fluorescently labeled hybridizing probe and said first primer and said second primer to yield increasing levels of fluorescence signal above fluorescence background;
    wherein said amplification of said species-specific DNA indicates the presence of said viable microbial cells in said one or more samples,
    wherein at least one of said first primer, said second primer or said probe comprise nucleic acids complementary to the mRNA of the Elongation Factor 3 gene, and
    wherein said quantitation of said amplified species-specific DNA provides a relative measurement of the amount of said viable microbial cells in said one or more samples.

2. The method of claim 1, wherein said microorganism of interest is selected from the group consisting of *Escherichia coli*, *Serratia marcescens*, and *Bacillus subtilis*, and further wherein said first primer, said second primer, and said fluorescently labeled hybridizing probe are designed on the 3'-end of 16S rRNA.

3. The method of claim 1, wherein said microorganism of interest is selected from the group consisting of *Pseudomonas aeruginosa*, *Staphylococcus aureus*, and *Staphylococcus epidermidis*, and further wherein said first primer, said second primer, and said fluorescently labeled hybridizing probe are designed on the 5'-end of 23S rRNA.

4. The method of claim 1, wherein said microorganism of interest is *Aspergillus brasiliensis*, and further wherein said first primer, said second primer, and said fluorescently labeled hybridizing probe are designed on the 5'-end of 5.8S rRNA.

5. The method of claim 1, further comprising:
    collecting cells onto a filter membrane and
    lysing said collected cells.

6. The method of claim 1, further comprising:
    applying said amplification step and said quantitation step to both a test sample and a control sample, wherein said control sample contains non-treated cells; and
    comparing the relative measurement of the amount of said viable microbial cells in said control samples to the relative measurement of the amount of said viable microbial cells in said test sample.

7. The method of claim 1, wherein said one or more samples contains one or more cell culture formulations or preservatives in need of screening or efficacy testing.

8. A method for identifying and quantifying viable microbial cells in one or more samples containing a microorganism of interest, comprising:
    (a) amplification of species-specific DNA from Elongation Factor 3 (EF-3) mRNA-containing samples using a reverse transcription-polymerase chain reaction, said amplification step comprising:
        using a forward primer complementary to the EF-3 pre-rRNA region of said microorganism of interest;
        using a reverse primer complementary to the EF-3 mature rRNA region of said microorganism of interest; and
        performing multiple cycles of amplification using said forward primer and said reverse primer to yield detectable levels of amplified species-specific DNA; and
    (b) quantitation of said amplified species-specific DNA, said quantitation step comprising:
        using a fluorescently labeled forward hybridizing probe complementary to said EF-3 mature rRNA region of said microorganism of interest;
        using said forward primer complementary to said EF-3 pre-rRNA region of said microorganism of interest;
        using said reverse primer complementary to said EF-3 mature rRNA region of said microorganism of interest; and
        performing multiple cycles of amplification using said fluorescently labeled forward hybridizing probe and said forward primer and said reverse primer to yield increasing levels of fluorescence signal above fluorescence background;
    wherein said amplification of said species-specific DNA indicates the presence of said viable microbial cells in said one or more samples, and
    wherein said quantitation of said amplified species-specific DNA provides a relative measurement of the amount of said viable microbial cells in said one or more samples.

9. The method of claim 8, wherein said microorganism of interest is *Candida albicans*.

10. The method of claim 8, further comprising:
    collecting cells onto a filter membrane and
    lysing said collected cells.

11. The method of claim 8, further comprising:
    applying said amplification step and said quantitation step to both a test sample and a control sample, wherein said control sample contains non-treated cells; and
    comparing the relative measurement of the amount of said viable microbial cells in said control samples to the relative measurement of the amount of said viable microbial cells in said test sample.

12. The method of claim 8, wherein said one or more samples contains one or more cell culture formulations or preservatives in need of screening or efficacy testing.

13. A method of cell culture formulation screening or cell culture preservative efficacy testing, comprising:
   calibrating cells to a desired density;
   collecting cells on a filter membrane;
   applying nutrients to said membrane to yield enriched cells;
   incubating said enriched cells;
   removing nutrients;
   adding lysis buffer to membrane;
   recovering cell lysates;
   transferring lysate;
   extracting and purifying RNA; and
   amplifying and quantitating species-specific DNA by the reverse transcription-polymerase chain reaction according to the method of claim 1.

14. A kit, comprising:
   at least one primer pair ("primers"), said primers comprising a first primer that hybridizes to a bacteria pre-rRNA region and a second primer that hybridizes to a bacteria mature rRNA region;
   said primers combined with at least one probe, wherein said probe hybridizes to said bacteria mature rRNA region between said first primer and said second primer;
   wherein at least one of said primers or said at least one probe comprise nucleic acids complementary to the 3'-end of 16S rRNA, nucleic acids complementary to the 5'-end of 23S rRNA, or nucleic acids complementary to the 5'-end of 5.8S rRNA; wherein at least one of said primers or said at least one probes comprise nucleic acids complementary to the mRNA of the Elongation Factor 3 gene; and
   wherein at least one of said primers or said at least one probe further comprise at least one non-natural label.

15. A kit for identifying and quantifying viable microbial cells in one or more samples containing a microorganism of interest, comprising:
   at least one primer pair ("primers"), said primers comprising a first primer that hybridizes to a pre-rRNA region and a second primer that hybridizes to a mature rRNA region;
   said primers combined with at least one probe, wherein said probe hybridizes to said mature rRNA region between said first primer and said second primer;
   wherein at least one of said primers or said at least one probes comprise nucleic acids complementary to the mRNA of the Elongation Factor 3 gene and
   wherein at least one of said primers or said at least one probe further comprise at least one non-natural label.

16. A method of cell culture formulation screening or cell culture preservative efficacy testing, comprising:
   calibrating cells to a desired density;
   collecting cells on a filter membrane;
   applying nutrients to said membrane to yield enriched cells;
   incubating said enriched cells;
   removing nutrients;
   adding lysis buffer to membrane;
   recovering cell lysates;
   transferring lysate;
   extracting and purifying RNA; and
   amplifying and quantitating species-specific DNA by the reverse transcription-polymerase chain reaction according to the method of claim 8.

17. The kit of claim 14, further comprising:
   instructions outlining use of kit for identifying and quantifying viable microbial cells in one or more samples containing a microorganism of interest.

18. The kit of claim 15, further comprising:
   instructions outlining use of kit for identifying and quantifying viable microbial cells in one or more samples containing a microorganism of interest.

19. A kit for detecting microorganisms in a sample, comprising:
   first primers directed to precursor regions of rRNAs;
   second primers directed to mature regions of rRNAs; and
   probes directed to mature region of rRNAs;
   wherein said first primers and said second primers are combined with said probes; and
   wherein at least one of said first primers, said second primers, or said probes further comprises at least one non-natural label;
   wherein at least one of said first primers, said second primers or said probes comprise nucleic acids complementary to the 3'-end of bacteria 16S rRNA, nucleic acids complementary to the 5'-end of bacteria 23S rRNA, or nucleic acids complementary to the 5'-end of bacteria 5.8S rRNA;
   wherein at least one of said primers or said at least one probes comprise nucleic acids complementary to the mRNA of the Elongation Factor 3 gene; and
   instructions outlining use of kit for identifying and quantifying said microorganism in said sample.

* * * * *